US006835184B1

(12) United States Patent
Sage et al.

(10) Patent No.: US 6,835,184 B1
(45) Date of Patent: *Dec. 28, 2004

(54) METHOD AND DEVICE FOR ABRADING SKIN

(75) Inventors: Burton H. Sage, Raleigh, NC (US); Carl Randolph Bock, Durham, NC (US)

(73) Assignee: Becton, Dickinson and Company, Franklin Lakes, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/405,488

(22) Filed: Sep. 24, 1999

(51) Int. Cl.[7] .............................................. A61B 17/20
(52) U.S. Cl. ........................... 604/46; 604/47; 604/20; 604/272
(58) Field of Search ............................ 604/20, 46, 47, 604/239, 272, 890.1

(56) References Cited

U.S. PATENT DOCUMENTS

| | | | |
|---|---|---|---|
| 3,964,482 A | * 6/1976 | Gerstel et al. | 604/890.1 |
| 4,538,612 A | * 9/1985 | Patrick, Jr. | 606/131 |
| 5,003,987 A | 4/1991 | Grinwald | 128/734 |
| 5,091,379 A | * 2/1992 | Aungst | 514/159 |
| 5,120,542 A | * 6/1992 | Scher et al. | 424/405 |
| 5,250,023 A | 10/1993 | Lee et al. | |
| 5,273,528 A | 12/1993 | Skeen et al. | 604/47 |
| 5,383,848 A | * 1/1995 | Hillman et al. | 604/20 |
| 5,501,784 A | 3/1996 | Lessmollmann et al. | 205/67 |
| 5,611,806 A | 3/1997 | Jang | |
| 5,660,680 A | 8/1997 | Keller | 438/50 |
| 5,679,647 A | 10/1997 | Carson et al. | 514/44 |
| 5,685,515 A | 11/1997 | Lee et al. | 264/219 |
| 5,848,991 A | 12/1998 | Gross et al. | 604/140 |
| 5,855,801 A | 1/1999 | Lin et al. | 216/2 |
| 5,873,850 A | 2/1999 | Flower et al. | |
| 5,879,326 A | 3/1999 | Godshall et al. | |

(List continued on next page.)

FOREIGN PATENT DOCUMENTS

| | | | |
|---|---|---|---|
| EP | 0 381 410 A1 | 8/1990 | A61B/17/20 |
| EP | 0 509 122 B1 | 10/1996 | A61N/1/30 |
| EP | 1 092 444 A1 | 4/2001 | A61M/5/46 |
| RU | 172 4181 | 4/1992 | A61B/10/00 |
| WO | WO97/03718 | 7/1995 | |
| WO | WO 96/07369 | 3/1996 | A61D/1/02 |
| WO | WO96/37256 | 5/1996 | |
| WO | WO/97/11650 | 9/1996 | |
| WO | WO 97/48440 | 12/1997 | |
| WO | WO 97/48442 | 12/1997 | A61N/1/30 |
| WO | WO 98/00193 | 1/1998 | A61M/31/00 |
| WO | WO 99/00155 | 1/1999 | A61M/5/32 |
| WO | WO 99/43350 | 9/1999 | A61K/39/39 |

OTHER PUBLICATIONS

Dizon, et al., An Ion Milling Pattern Transfer Technique for Fabrication of Three–Dimensional Micromechanical Structures, Journal of Microelectro Mechanical Systems, vol. 2, No. 4, pp. 151–159 Dec. 1993.

Primary Examiner—Brian L. Casler
Assistant Examiner—Jeremy Thissell
(74) Attorney, Agent, or Firm—Eric M. Lee; Robert E. West

(57) ABSTRACT

A device includes a plurality of microneedles for abrading the stratum corneum of the skin to form a plurality of grooves in the tissue having a controlled depth and width. The microneedles have a length of about 5–250 microns and generally about 5–200 microns. The device is rubbed over the skin to prepare an abraded site after which a transdermal delivery or sampling device is applied to the abraded delivery site. The abrasion increases the permeability of the skin and the rate of delivery and extraction of a substance without pain or irritation to the patient.

25 Claims, 13 Drawing Sheets

U.S. PATENT DOCUMENTS

| | | | | |
|---|---|---|---|---|
| 5,882,677 | A | 3/1999 | Kupperblatt | |
| 5,885,211 | A | 3/1999 | Eppstein et al. | 600/309 |
| 5,895,369 | A | 4/1999 | Flower | |
| 5,899,876 | A | 5/1999 | Flower | |
| 5,910,306 | A | 6/1999 | Alving et al. | 424/184.1 |
| 5,919,364 | A | 7/1999 | Lebouitz et al. | 210/321.84 |
| 5,928,207 | A | 7/1999 | Pisano et al. | 604/272 |
| 5,931,794 | A | 8/1999 | Pitesky | 600/556 |
| 5,958,589 | A | 9/1999 | Glenn et al. | 428/402.2 |
| 5,970,998 | A | 10/1999 | Talbot et al. | 137/1 |
| 5,980,898 | A | 11/1999 | Glenn et al. | 424/184.1 |
| 6,015,599 | A | 1/2000 | Keller et al. | 428/34.4 |
| 6,050,988 | A * | 4/2000 | Zuck | 604/20 |
| 6,065,864 | A | 5/2000 | Evans et al. | 366/167.1 |
| 6,106,751 | A | 8/2000 | Talbot et al. | 264/81 |
| 6,132,755 | A * | 10/2000 | Eicher et al. | 424/427 |
| 6,173,202 | B1 | 1/2001 | Eppstein | 604/20 |
| 6,183,434 | B1 * | 2/2001 | Eppstein | 604/22 |
| 6,187,210 | B1 | 2/2001 | Lebouitz et al. | 216/11 |
| 6,211,243 | B1 * | 4/2001 | Johnson | 514/634 |
| 6,230,051 | B1 * | 5/2001 | Cormier et al. | 604/20 |
| 6,231,540 | B1 * | 5/2001 | Smedegaard | 604/239 |
| 6,256,533 | B1 * | 7/2001 | Yuzhakov et al. | 604/20 |
| 6,312,612 | B1 | 11/2001 | Sherman et al. | 216/2 |
| 6,334,856 | B1 | 1/2002 | Allen et al. | 604/191 |

* cited by examiner

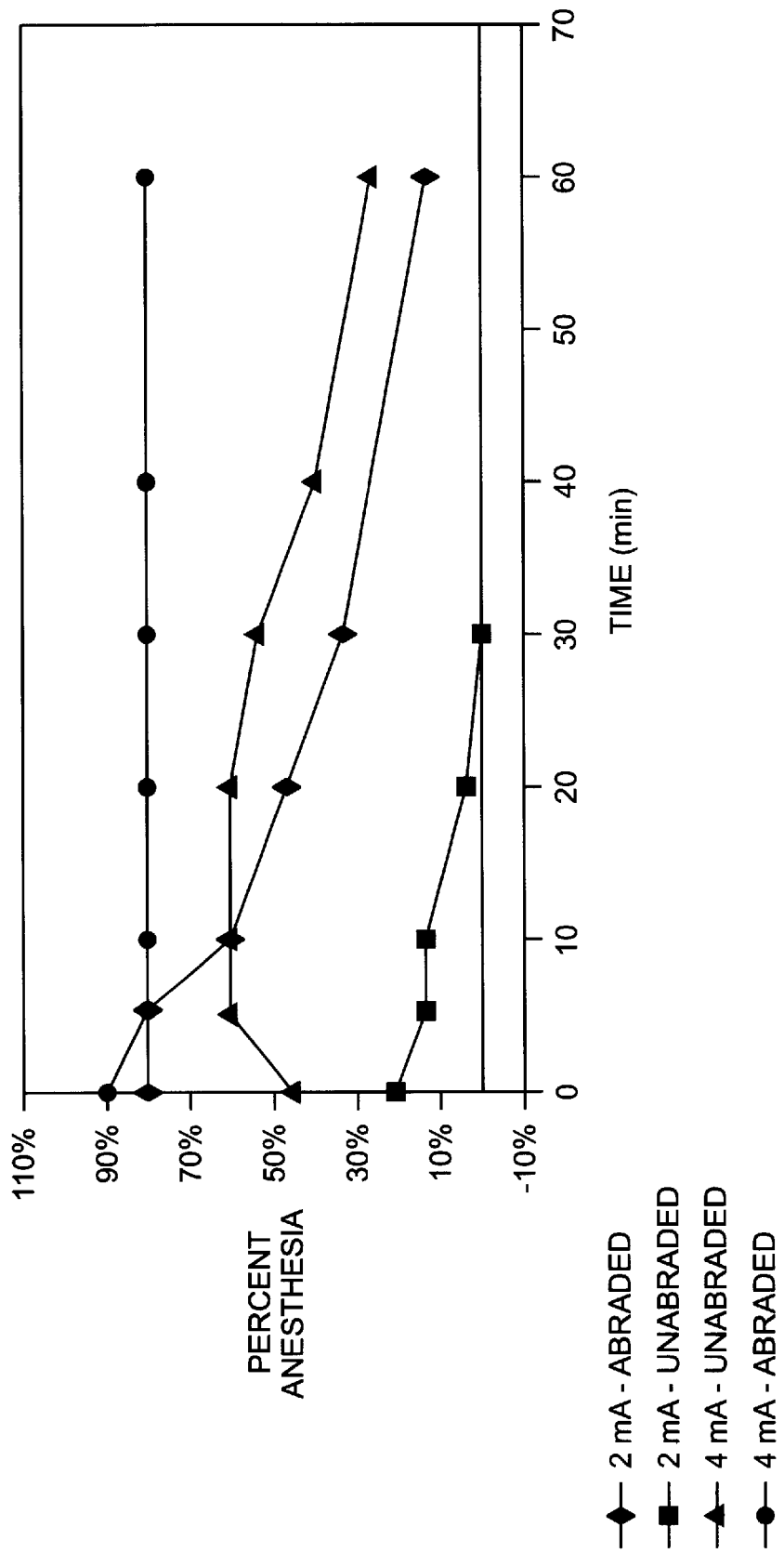

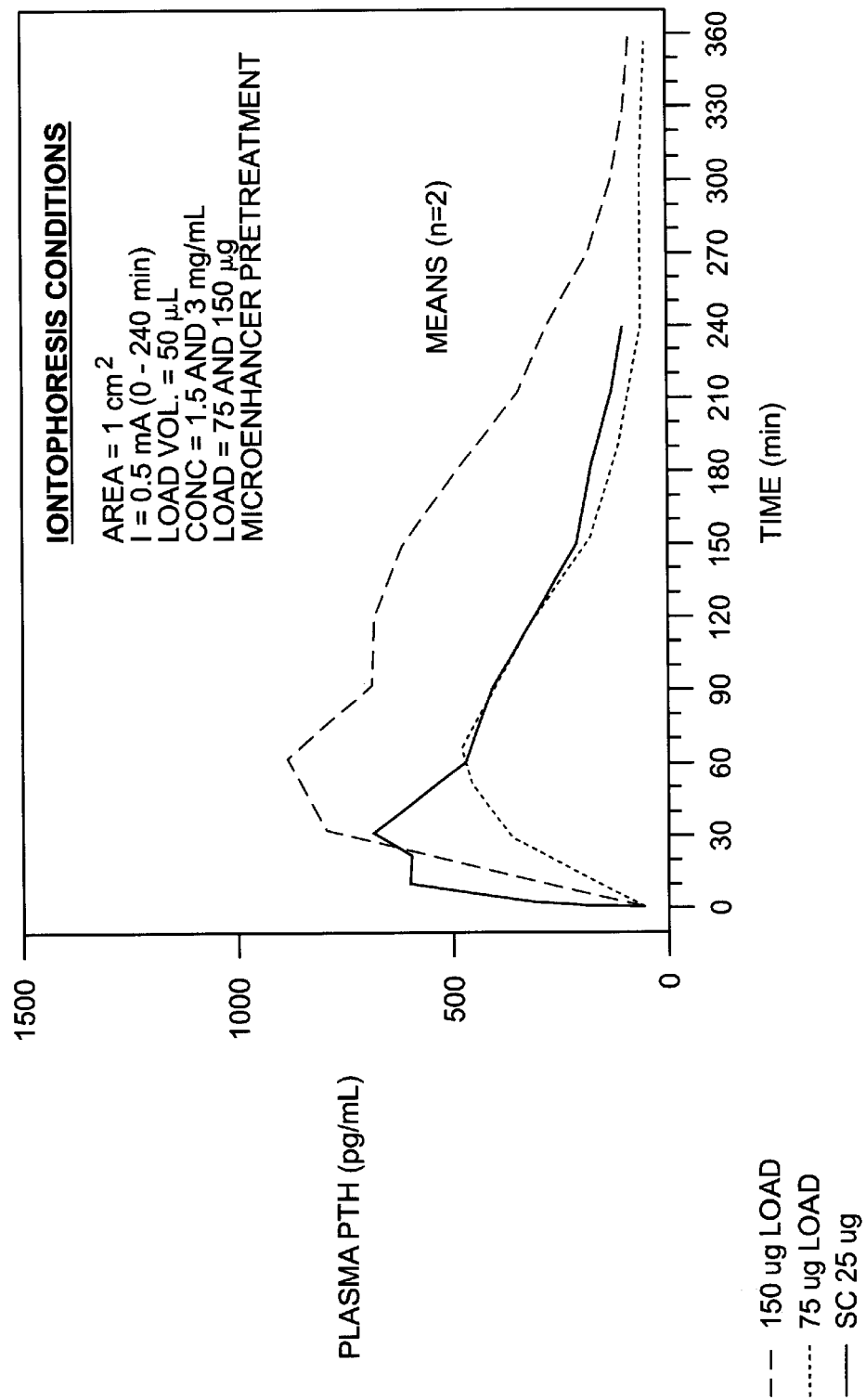

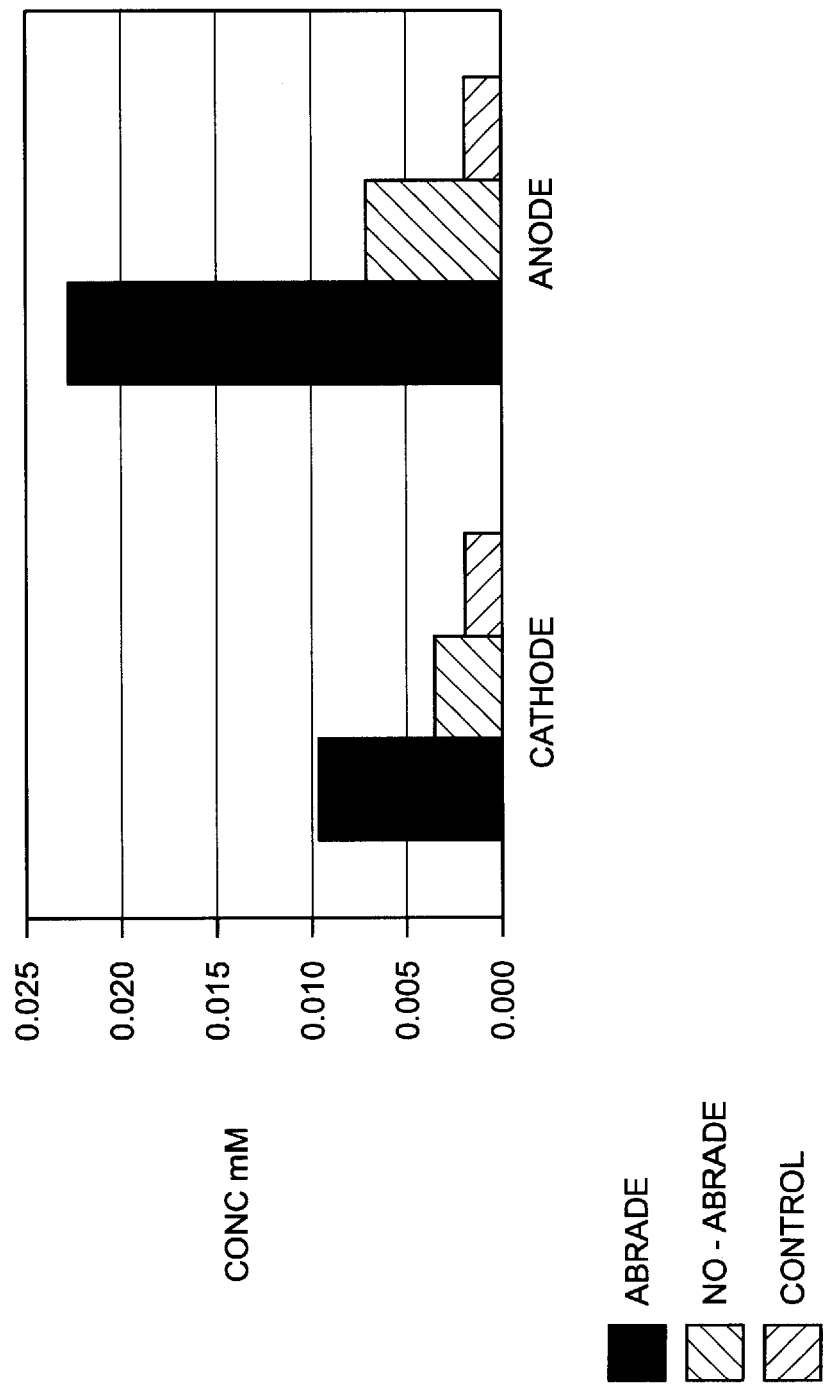
FIG-12  EXTRACTION FROM PATCHES ISF

METHOD AND DEVICE FOR ABRADING SKIN

FIELD OF THE INVENTION

The present invention relates to a method and device for abrading the skin. More particularly, the invention is directed to a method of abrading the stratum corneum to promote transdermal delivery or sampling of a substance.

BACKGROUND OF THE INVENTION

The skin is made up of several layers with the upper composite layer being the epithelial layer. The outermost layer of the skin is the stratum corneum that has well known barrier properties to prevent external molecules and various substances from entering the body and internal substances from exiting the body. The stratum corneum is a complex structure of compacted keratinized cell remnants having a thickness of about 10–30 microns. The stratum corneum forms a hydrophobic membrane to protect the body from invasion by various substances and to prevent the outward migration of various compounds.

The natural impermeability of the stratum corneum inhibits the administration of most pharmaceutical agents and other substances through the skin. Numerous methods and devices have been proposed to enhance the permeability of the skin and to increase the diffusion of various drugs through the skin so that the drugs can be utilized by the body. Typically, the delivery of drugs through the skin is enhanced by either increasing the permeability of the skin or increasing the force or energy used to direct the drug through the skin.

Several methods of enhancing skin permeability have been proposed and used with varying success. The prior mechanical methods use an adhesive strip that is repeatedly applied to the skin to strip numerous layers of cells from the stratum corneum. Other methods use a scraper such as a scalpel blade or sandpaper to abrade the skin. These methods are usually painful or uncomfortable and increase the risk of infection by excessively reducing the skin barrier function.

Other methods of increasing skin permeability use various chemical permeation enhancers or electrical energy such as electroporation. Ultrasonic energy such as sonophoresis and laser treatments has been used. These methods require complex and energy intensive electronic devices that are relatively expensive. The chemical enhancers are often not suitable for transdermal drug delivery or sampling.

One example of a method for increasing the delivery of drugs through the skin is iontophoresis. Iontophoresis generally applies an external electrical field across the skin. Ionic molecules in this field are moved across the skin due to the force of the electric field. The amount and rate of drug delivery using iontophoresis can be difficult to control. Iontophoresis can also cause skin damage on prolonged exposure.

Sonic, and particularly ultrasonic energy, has also been used to increase the diffusion of drugs through the skin. The sonic energy is typically generated by passing an electrical current through a piezoelectric crystal or other suitable electromechanical device. Although numerous efforts to enhance drug delivery using sonic energy have been proposed, the results generally show a low rate of drug delivery.

Another method of delivering drugs through the skin is by forming micropores or cuts through the stratum corneum. By piercing the stratum corneum and delivering the drug to the tissue below the stratum corneum, many drugs can be effectively administered. The devices for piercing the stratum corneum generally include a plurality of micron-size needles or blades having a length to pierce the stratum corneum without passing completely through the epidermis. Examples of these devices are disclosed in U.S. Pat. No. 5,879,326 to Godshall et al.; U.S. Pat. No. 5,250,023 to Lee et al.; and WO 97/48440.

Transdermal drug delivery is also known to use pulsed laser light to ablate the stratum corneum without significant ablation or damage to the underlying epidermis. A drug is then applied to the ablated area and allowed to diffuse through the epidermis.

The prior methods and apparatus for the transdermal administration of drugs have exhibited limited success. Accordingly, a continuing need exists in the industry for an improved device for the transdermal administration of various drugs and other substances.

SUMMARY OF THE INVENTION

The present invention is directed to a method and device for abrading the skin, and particularly, the stratum corneum of the skin. The invention is further directed to a method of obtaining a sample or for the transdermal delivery of a substance, such as a drug or pharmaceutical agent, through the abraded area on the stratum corneum. One aspect of the invention is directed to a method and device for preparing a delivery site on the skin to enhance the delivery of a pharmaceutical agent through the stratum corneum of the skin to a sufficient depth where the pharmaceutical agent can be absorbed and utilized by the body.

To clarify this invention, two definitions are made. Penetrate, in the context of this invention, shall mean to enter, but not pass through a body or substrate. Pierce, in the context of this invention, shall mean to enter and pass through the body or substrate Accordingly, a primary object of the invention is to provide a method and device for efficiently penetrating the stratum corneum substantially without pain to the patient and with a minimum of irritation to skin, thereby exposing the tissue below the stratum corneum directly to a pharmaceutical agent for absorption by the body.

A further object of the invention is to provide a method for abrading the stratum corneum in a simple and reliable manner.

Another object of the invention is to provide a microabrader device having a plurality of microneedles which when rubbed on the skin penetrate the stratum corneum and form a plurality of spaced-apart grooves in the stratum corneum.

A further object of the invention is to provide a device for delivering a plurality of drugs transdermally through an abraded area of the skin to a patient either simultaneously or sequentially.

Another object of the invention is to provide a method for transdermally delivering a substance through an abraded area of the skin using iontophoresis.

A further object of the invention is to provide a method and device for penetrating the stratum corneum and for the sampling of a substance from a patient.

A still further object of the invention is to provide a device having a plurality of microneedles for abrading and penetrating the stratum corneum and a supply for supplying a substance, such as a pharmaceutical agent, to the microneedles.

Another object of the invention is to provide a device having a plurality of microneedles having a blunt tip for abrading a plurality of grooves into the stratum corneum without piercing the stratum corneum.

Still another object of the invention is to provide an abrader and delivery device having an array of microneedles for abrading and penetrating the stratum corneum of the skin, where the device has a channel in a bottom surface for directing a substance to the microneedles and the abraded skin.

A further object of the invention is to provide a microabrader device having an array of microneedles for abrading the skin to transdermally withdraw a substance from the patient.

A further object of the invention is to provide a method and device for reducing the impedance of the skin without piercing the stratum corneum for measuring the body's internal electrical signals, such as EKG.

These and other objects of the invention are substantially achieved by providing a device for abrading the skin to promote the delivery or withdrawal of a substance through the skin of a patient. In a preferred embodiment, the device comprises a planar support having a bottom surface. A plurality of microneedles is coupled to and integral with the bottom surface of the support. The microneedles have a blunt, flat tip and a length sufficient to penetrate the stratum corneum of the skin without piercing the stratum corneum during abrading of the skin to enhance the permeability of the skin.

The objects and advantages of the invention are further attained by providing a method for intradermal delivery of a substance to a patient. The method comprises positioning a microabrader at a delivery site on the skin of a patient where the microabrader has a planar support and a plurality of microneedles coupled to the planar support. The microneedles have a length to penetrate the stratum corneum of the skin without piercing the stratum corneum. The microabrader is moved over the surface of the skin to abrade the stratum corneum on the delivery site and thereafter a substance is applied to the delivery site for transferring through the skin for absorption by the body.

The objects of the invention are further attained by providing a method of treating the skin of a patient to enhance transdermal delivery of a substance or the withdrawal of a substance from the body. The method comprises positioning a microabrader with a plurality of microneedles at a delivery site on the skin of the patient and moving the microabrader in a direction to abrade the stratum corneum and form an abraded area. The abraded area has a plurality of grooves formed in the skin by abrasion with the microneedles and a peak between the grooves. The grooves penetrate, but do not pass through or pierce the stratum corneum.

The objects, advantages and other salient features of the invention will become apparent from the following detailed description which, taken in conjunction with the annexed drawings, discloses preferred embodiments of the invention.

BRIEF DESCRIPTION OF THE DRAWINGS

The following is a brief description of the drawings, in which:

FIG. 10 is a graph comparing the anesthesia in relation to the current in an iontophoretic device on abraded and unabraded sites;

FIG. 11 is a graph showing the plasma concentration of PTH by iontophoresis and subcutaneous injection; and FIG. 12 is a graph showing concentration of fluorescein extracted from sampling sites by iontophoresis.

DETAILED DESCRIPTION OF THE PREFERRED EMBODIMENTS

Figure 1:
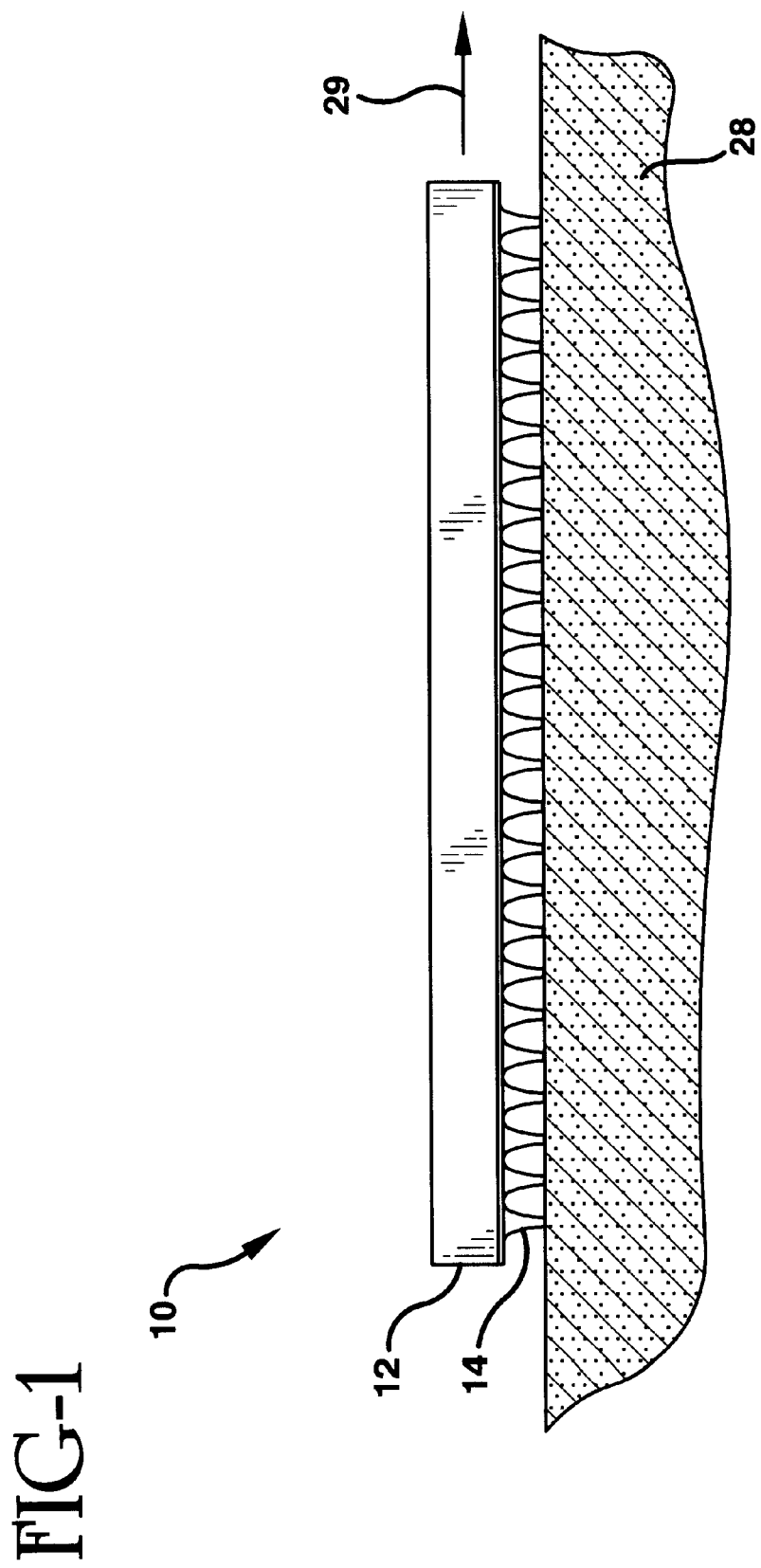
FIG. 1 is an end view of a microabrader positioned on the skin in accordance with one embodiment of the invention.

The present invention is directed to a method and device for preparing the skin for transdermally administering a substance to the body of a patient, withdrawing a substance from the body of a patient, or making a measurement of an electrical signal generated inside the body. More particularly, the invention is directed to a device and to a method for abrading the stratum corneum to enhance the administering of a substance through the stratum corneum of the skin of a patient.

As used herein, the term abrade refers to removing at least a portion of the stratum corneum to increase the permeability of the skin without causing excessive skin irritation or compromising the skin's barrier to infectious agents. The microabrader of the invention is a device capable of abrading the skin to attain this result. In preferred embodiments, the abrading of the skin penetrates the stratum corneum without piercing the stratum corneum. As used herein, penetrating refers to entering the stratum corneum without passing completely through the stratum corneum into the adjacent layers. Piercing refers to passing through the stratum corneum into the adjacent layers below the stratum corneum.

The device and method of the present invention are particularly suitable for use in preparing skin to reduce the electrical resistance for measuring an electrical signal generated in the body, administering a substance, such as a pharmaceutical agent, to a patient or withdrawing a substance transdermally from a patient. As used herein, a pharmaceutical agent includes a substance having biological activity. Examples of suitable pharmaceutical agents which can be delivered through the body membranes and surfaces, and particularly the skin, include antibiotics, antiviral agents, analgesics, anesthetics, anorexics, antiarthritics, antidepressants, antihistamines, anti-inflammatory agents, antineoplastic agents, vaccines (including DNA vaccines), and the like. Other substances that can be delivered intradermally to a patient include proteins, peptides and fragments thereof. The proteins and peptides can be naturally occurring, synthesized or recombinantly produced. Substances and agents withdrawn from the body include analytes, drugs, glucose, body electrolytes, alcohol, blood gases, and the like. Signals measured on an abraded skin site include EKG and EEG signals.

The method of the invention is primarily directed to preparing the skin and particularly the stratum corneum using the abrader device for enhancing the delivery of a substance transdermally to a patient and for sampling various agents from the patient. In one embodiment of the invention, the device is applied and moved or rubbed on the skin to abrade and remove a portion of the stratum corneum substantially without piercing the stratum corneum. The device is removed and an active or passive drug delivery device, or sampling device, or signal electrode is then applied over the abraded area.

It has been found that the preparation of the skin by abrading a portion of the stratum corneum provides a significant increase in the rate of delivery and dose of a substance through the stratum corneum compared to conventional active and passive transdermal delivery devices. Abrasion of the skin according to the invention provides an increased rate of delivery of a substance compared to the use of chemical enhancers for passive delivery. The most notable increase in delivery is found by iontophoresis on a previously abraded delivery site.

In some embodiments of the present invention, a vaccine is administered using the device and method of the invention. The microabrader device of the invention is believed to have a unique immunological advantage in the delivery of vaccines with the potential of increasing the vaccine's clinical value. The penetration of the multiple needle ends into the stratum corneum is suggested as having an adjuvant-like stimulatory effect. The needlestick response from multiple microneedle points is believed more than a simple acute inflammatory response. Needlesticks can cause damage to a variety of cells and cellular architecture, causing the appearance of polymorphonuclear neutrophils (PMN) and macrophages as well as the release of ILI, tumor necrosis factor (TNF) and other agents, which can lead to a number of other immunological responses. The soluble stimulatory factors influence the proliferation of lymphocytes and are central to the immune response to vaccines. The immune stimulation is proportional to the direct needle-cell interaction.

The microabrader of the present invention is valuable in promoting significant immune response to a vaccine in the abraded area. The small grooves created by the microneedle array over the abraded area are believed to increase the availability of the vaccine antigen for interaction with antigen presenting cells compared to a vaccine deposited by standard needles.

The microneedle array of the invention is believed to magnify several-fold the trivial or inconsequential immune stimulatory impact of a single needlestick. The microabrader facilitates and enhances vaccine immunogenicity by an adjuvant-like immune stimulation.

The primary barrier properties of the skin including the resistance to drug delivery reside in the outermost layer of the epidermis, referred to as the stratum corneum. The inner layers of the epidermis generally include three layers, commonly identified as the stratum granulosum, the stratum malpighii, and the stratum germinativum. Once a drug or other substance appears below the stratum corneum, there is essentially no resistance to diffusion into subsequent layers of the skin and eventual absorption by the body. Helping a substance into the stratum corneum can be an effective method for facilitating absorption of some substances, and particularly some vaccines, by the body. The present invention is primarily directed to a device and method for facilitating delivery of a substance, and particularly a pharmaceutical agent, into the stratum corneum for more rapid absorption of larger quantities of the substance or pharmaceutical agent by the patient. Preferably, the device of the invention penetrates, but does not pierce, the stratum corneum.

Referring to FIG. 1, the microabrader device 10 of the invention includes a substantially planar body or support 12 having a plurality of microneedles 14 extending from the bottom surface of the support. The support generally has a thickness sufficient to provide rigidity to the device and to allow the device to be handled easily. Alternatively, a handle or gripping device can be attached to the top surface of the support 12. The dimensions of the support 12 can vary depending on the length of the microneedles, the number of microneedles in a given area and the amount of the substance to be administered to the patient. Typically, the support 12 has a surface area of about 1–4 cm$^2$. In preferred embodiments, the support surface 12 has a surface area of about 1 cm$^2$.

Figure 2:
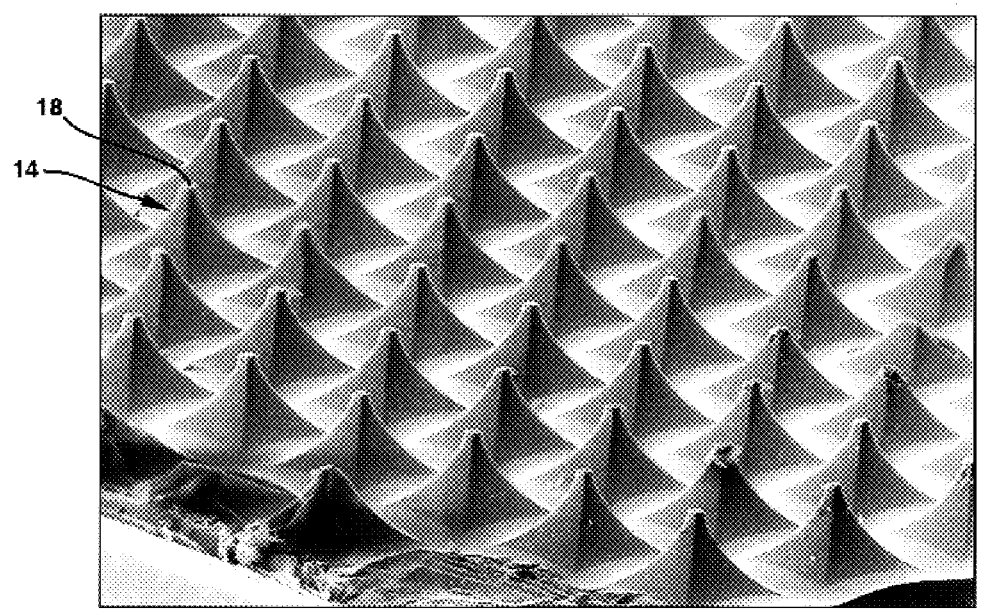
FIG. 2 is a perspective view of the microabrader surface in the embodiment of FIG. 1.
Figure 2A:
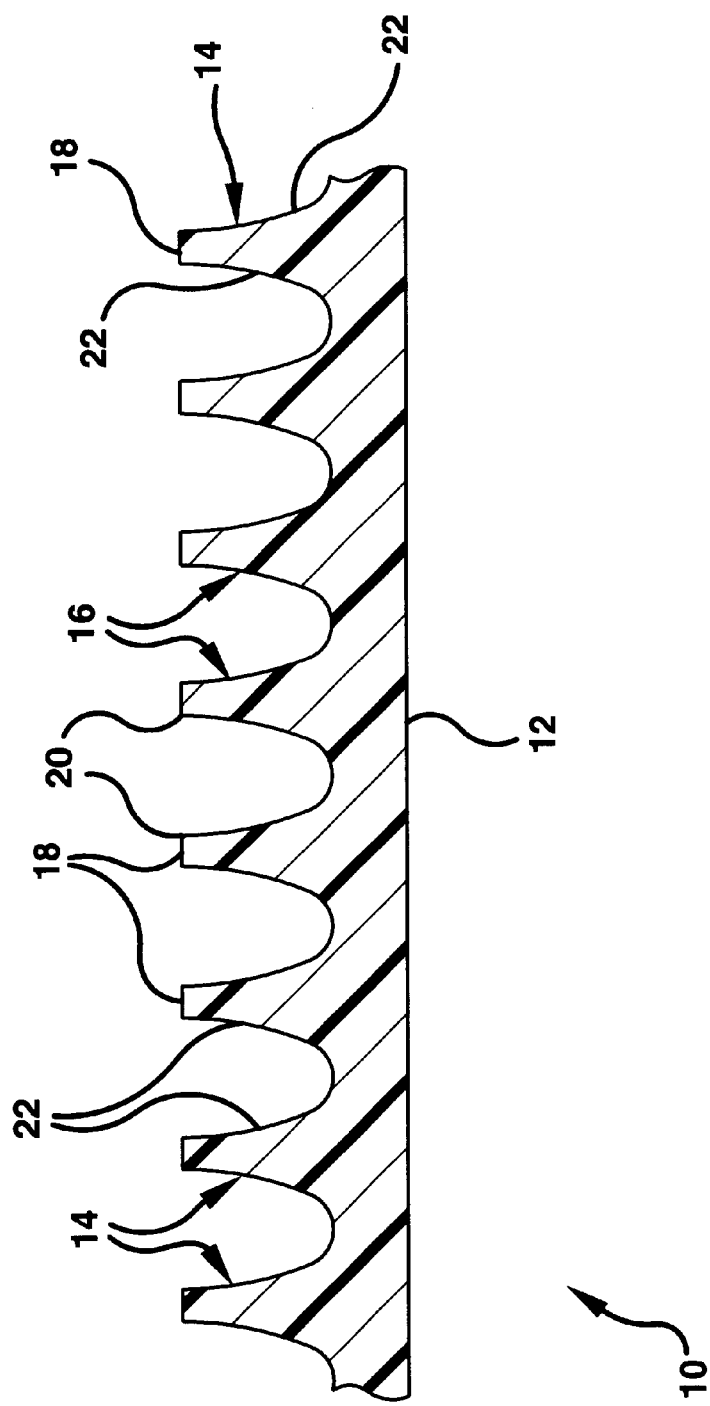
FIG. 2A is a cross-sectional side view of the microabrader.
Figure 3:
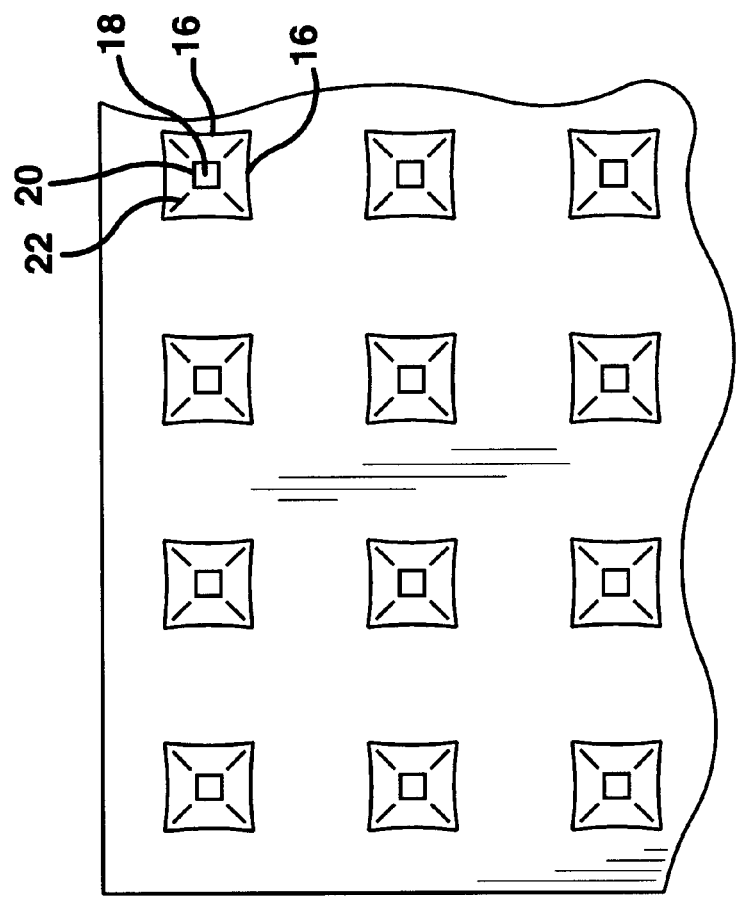
FIG. 3 is a bottom view of the microabrader in the embodiment of FIG. 1 showing the tips of the microneedles.

As shown in FIGS. 1, 2 and 2A, the microneedles 14 are attached to the surface of the support 12 and extend substantially perpendicular to the plane of the support 12. The microneedles in the illustrated embodiment are arranged in a plurality of rows and columns and are preferably spaced apart a uniform distance. The microneedles 14 have a generally pyramid shape with sides 16 extending to a tip 18. The sides 16 as shown have a generally concave profile when viewed in cross-section and form a curved surface extending from the support 12 to the tip 18. In the embodiment illustrated, the microneedles are formed by four sides 16 of substantially equal shape and dimension. As shown in FIG. 2, each of the sides 16 of the microneedles 14 have opposite side edges contiguous with an adjacent side and form a scraping edge 22 extending outward from the support 12. The scraping edges 22 define a generally triangular or trapezoidal scraping surface corresponding to the shape of the side 16. In further embodiments, the microneedles 14 can be formed with fewer or more sides. Alternatively, the microneedles can be conical, cylindrical with conical or pointed tips, blades, or other cutting devices.

The microneedles 14 preferably terminate at blunt tips 18. Generally, the tip 18 is substantially flat and parallel to the support 14. The tip 18 preferably forms a well defined, sharp edge 20 where it meets the sides 16. The edge 20 extends substantially parallel to the support 12 and defines a further scraping edge. In further embodiments, the edge 20 can be slightly rounded to form a smooth transition from the sides 16 to the tip 18.

The microabrader device 10 and the microneedles can be made from a plastic material that is non-reactive with the substance being administered. Suitable plastic materials include, for example, polyethylene, polypropylene, polyamides, polystyrenes, polyesters, and polycarbonates as known in the art. Alternatively, the microneedles can be made from a metal such as stainless steel, tungsten steel, alloys of nickel, molybdenum, chromium, cobalt, titanium, and alloys thereof, or other materials such as silicon, ceramics and glass polymers. Metal microneedles can be manufactured using various techniques similar to photolithographic etching of a silicon wafer or micromachining using a diamond tipped mill as known in the art.

The length and thickness of the microneedles are selected based on the particular substance being administered and the thickness of the stratum corneum in the location where the device is to be applied. Preferably, the microneedles penetrate the stratum corneum substantially without piercing or passing through the stratum corneum. The microneedles can have a length up to about 250 microns. Suitable microneedles have a length of about 5 to 200 microns. Typically, the microneedles have a length of about 50 to about 200 microns, and generally in the range of about 75 to 125 microns. The microneedles in the illustrated embodiment have a generally pyramidal shape and are perpendicular to the plane of the device. In preferred embodiments, the microneedles are solid members. In alternative embodiments, the microneedles can be hollow.

As shown in FIG. 2, the microneedles are typically spaced apart uniformly in rows and columns to form an array for contacting the skin and penetrating the stratum corneum during abrasion. The spacing between the microneedles can be varied depending on the substance being administered either on the surface of the skin or within the tissue of the skin. Typically, the rows of microneedles are spaced in rows to provide a density of about 2 to about 10 per millimeter (mm). Generally, the rows are spaced apart a distance substantially equal to the spacing of the microneedles in the row to provide a needle density of about 4 to about 100 needles per $mm^2$.

The method of preparing a delivery site on the skin places the microabrader against the skin 28 of the patient in the desired location. The microabrader is gently pressed against the skin and then pushed laterally in one direction in a substantially linear direction over or across the skin as indicated by the arrow 29 in FIG. 1. The length of the stroke of the microabrader can vary depending on the desired size of the delivery site defined by the abraded area. The dimensions of the delivery site are selected to accomplish the intended result and can vary depending on the substance being delivered. For example, the delivery site can cover a large area for treating a rash or skin disease. Generally, the microabrader is moved about 5 to 15 centimeters (cm), and preferably about 10 cm when a vaccine is to be delivered to the delivery site. In some embodiments of the invention, the microabrader is moved to produce an abraded site having a surface area of about 4 $cm^2$ to about 10 $cm^2$. The microabrader is then lifted from the skin to expose the abraded area and suitable transdermal delivery device is applied to the abraded area.

The extent of the abrasion of the stratum corneum is dependent on the pressure applied during movement and the number of repetitions with the microabrader. In one embodiment, the microabrader is lifted from the skin after making the first pass and placed back onto the starting position in substantially the same place and position. The microabrader is then pushed a second time in the same direction and for the same distance. Generally, two to three passes are made with the microabrader in the same direction. Generally, it is desirable to abrade the skin by making several passes on the skin by moving the microabrader only in one direction rather than in a back and forth motion. In further embodiments, the microabrader can be swiped in a grid-like pattern, a circular pattern, or in some other pattern for a time sufficient to abrade the stratum corneum a suitable depth to enhance the delivery of the desired substance substantially without piercing the stratum corneum.

Figure 4:
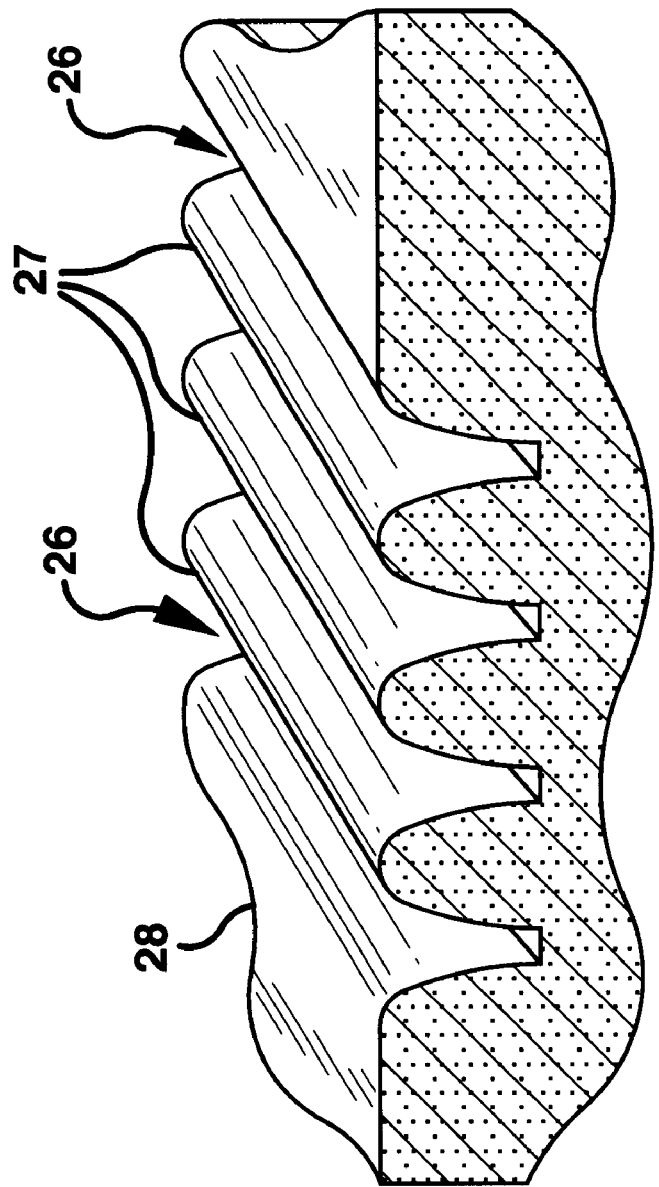
FIG. 4 is a perspective view in partial cross-section of the abraded skin showing the abraded grooves in the skin.
Figure 5:
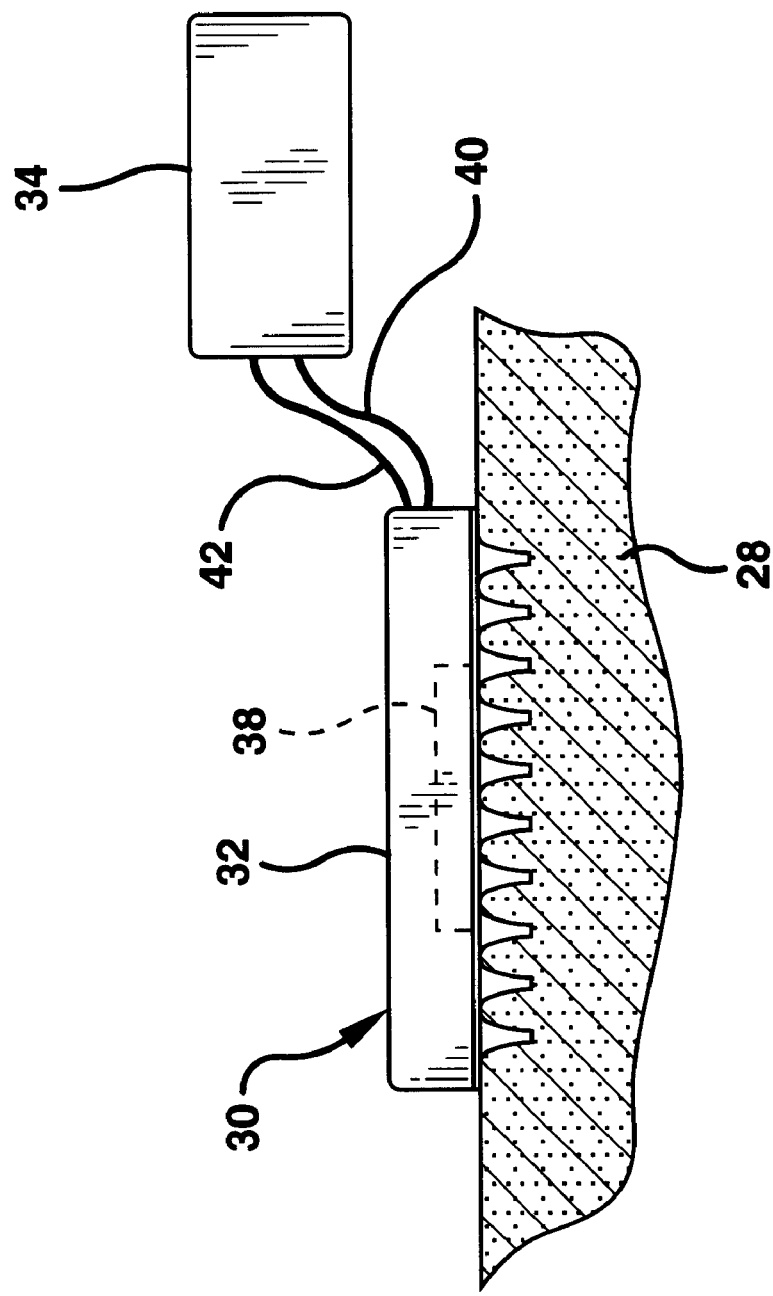
FIG. 5 is a side view of the abraded delivery site on the skin with an iontophoretic device placed on the abraded delivery site.

The linear movement of the microabrader across the skin 28 in one direction removes some of the tissue to form grooves 26, separated by peaks 27 in the skin 28 corresponding to substantially each row of microneedles as shown in FIG. 4. The edges 20, 22 and the blunt tip 18 of the microneedles provide a scraping or abrading action to remove a portion of the stratum corneum to form a groove or furrow in the skin rather than a simple cutting action. The edges 20 of the blunt tips 18 of the microneedles 14 scrape and remove some of the tissue at the bottom of the grooves 26 and allows them to remain open, thereby allowing the substance to enter the grooves for absorption by the body. Preferably, the microneedles 14 are of sufficient length to penetrate the stratum corneum and to form grooves 26 having sufficient depth to allow absorption of the substance applied to the abraded area without inducing pain or unnecessary discomfort to the patient. Preferably, the grooves 26 do not pierce or extend through the stratum corneum.

The edges 22 of the pyramid shaped microneedles 14 form scraping edges that extend from the support 12 to the tip 18. The edges 22 adjacent the support 12 form scraping surfaces between the microneedles which scrape and abrade the peaks 27 formed by the skin between the grooves 26. The peaks 27 formed between the grooves generally are abraded slightly.

The microabrader can be used to prepare a treatment site for measuring electrical signals from the body on the skin by reducing the electrical resistance in the stratum corneum. The microabrader can also be used to prepare a delivery site for the passive or active transdermal delivery of a substance into the delivery site for a time sufficient to allow the substance to diffuse into the abraded grooves 26 and through the stratum corneum for absorption into the body. The delivery device can be a conventional transdermal delivery device as known in the art. The delivery device can be a passive delivery patch relying primarily on the concentration of the substance to be delivered contained in the patch relative to the concentration in the delivery site. The delivery device can also be an active delivery device such as an iontophoretic device or an ultrasonic device, as known in the art. In a further embodiment, the device applied to the abraded site is a conducting pad for measuring electrical signals generated within the body.

In one embodiment, the transdermal delivery device is an iontophoretic drug delivery device 30 that is applied to the abraded delivery site. The iontophoretic device 30 includes a patch 32 and a controller 34. The patch 32 is generally a flexible member made of woven or non-woven textiles as known in the art. The patch 32 includes an adhesive layer covering at least a portion of the bottom surface to attach the patch 32 to the skin 28 of the patient. The bottom surface of the patch includes a reservoir 38 containing an ionic pharmaceutical agent that is typically in the form of a gel.

The patch 32 further contains a pair of electrodes that are positioned for contact with the skin 36 to provide an electric current path between the electrodes through the skin 36 of the patient when the patch 32 is adhesively attached to the skin 36. The electrodes are connected to leads 40, 42 that are coupled to the controller 34. One electrode is coupled to the reservoir 38 in a conventional manner as known in the art. A direct current is supplied from the controller 34 to the electrodes so that the electrode in contact with the reservoir 38 assumes the same charge as the ionized pharmaceutical contained therein. The influence of the electric current passing through the skin 36 from one electrode to the other causes the pharmaceutical agent from the reservoir 38 to pass transdermally through the skin 36. Examples of this kind of iontophoretic delivery system are disclosed in U.S. Pat. No. 5,895,369 to Flower, U.S. Pat. No. 5,899,876 to Flower, U.S. Pat. No. 5,882,677 to Kupperblatt, and U.S. Pat. No. 5,873,850 to Flower et al., all of which are hereby incorporated by reference in their entirety. In further embodiments, the delivery system can be another type of active or passive transdermal delivery system as known in the art.

In a further embodiment of the invention, the skin is prepared by abrading the stratum corneum according to the above method and an absorption or sampling device is then applied to the abraded site. The sampling device may be a conventional device such as a standard glucose sampling and monitoring patch as known in the art. Other sampling devices can be used to detect various analytes and drugs in the body.

It has been found that abrading the skin with the abraders of the invention enhances extraction of analytes through the skin during iontophoresis. Lightly abrading the skin to penetrate without piercing the stratum corneum can result in a three-fold enhancement of extraction of certain substances by iontophoresis compared to untreated skin. The abrasion generally produces little or no irritation at the treatment site. Abrading the skin prior to iontophoresis allows extraction of analytes from the skin with lower currents and shorter durations than can be obtained without abrasion. Normally, long periods of iontophoresis, especially at high current levels, can cause mild to moderate irritation. Abrading the skin prior to iontophoresis enhances the extraction of the same amount of a substance with milder iontophoretic conditions and less irritation to the patient.

In further embodiments, the microabrader can include a dried or lyophilized pharmaceutical agent on the support or on the microneedles. The dried pharmaceutical agent can be applied as a coating on the microneedles or in the valleys between the microneedles. During abrasion of the skin, the pharmaceutical agent is transferred to the abraded area of the skin. The microabrader can remain in place on the abraded delivery site for a sufficient time to allow the pharmaceutical agent to pass through the abraded delivery site into the stratum corneum. The microabrader can be attached to the skin by an adhesive tape or patch covering the microabrader. Preferably, the microabrader is attached to the abraded delivery site as prepared by the above method where the pharmaceutical agent is passively delivered without the use of a diluent or solvent.

In further embodiments, a suitable solvent or diluent such as distilled water or saline solution can be injected through an opening in the support to solubilize and reconstitute the pharmaceutical agent while the microabrader is attached to the delivery site. The solvent or diluent can be injected from a syringe or other container.

Typically, the microneedles are uniformly spaced apart to form an array and have a substantially uniform length and width. In a further embodiment, the microneedles have varying lengths to penetrate the skin at different depths. Varying the length of the microneedles allows the substance to be deposited at different depths in the stratum corneum and can increase the effectiveness of the delivery. The microneedles can have lengths ranging from about 50 microns to about 250 microns. In other embodiments, the array can have microneedles of several lengths ranging from about 50 microns to about 150 microns.

Figure 6:
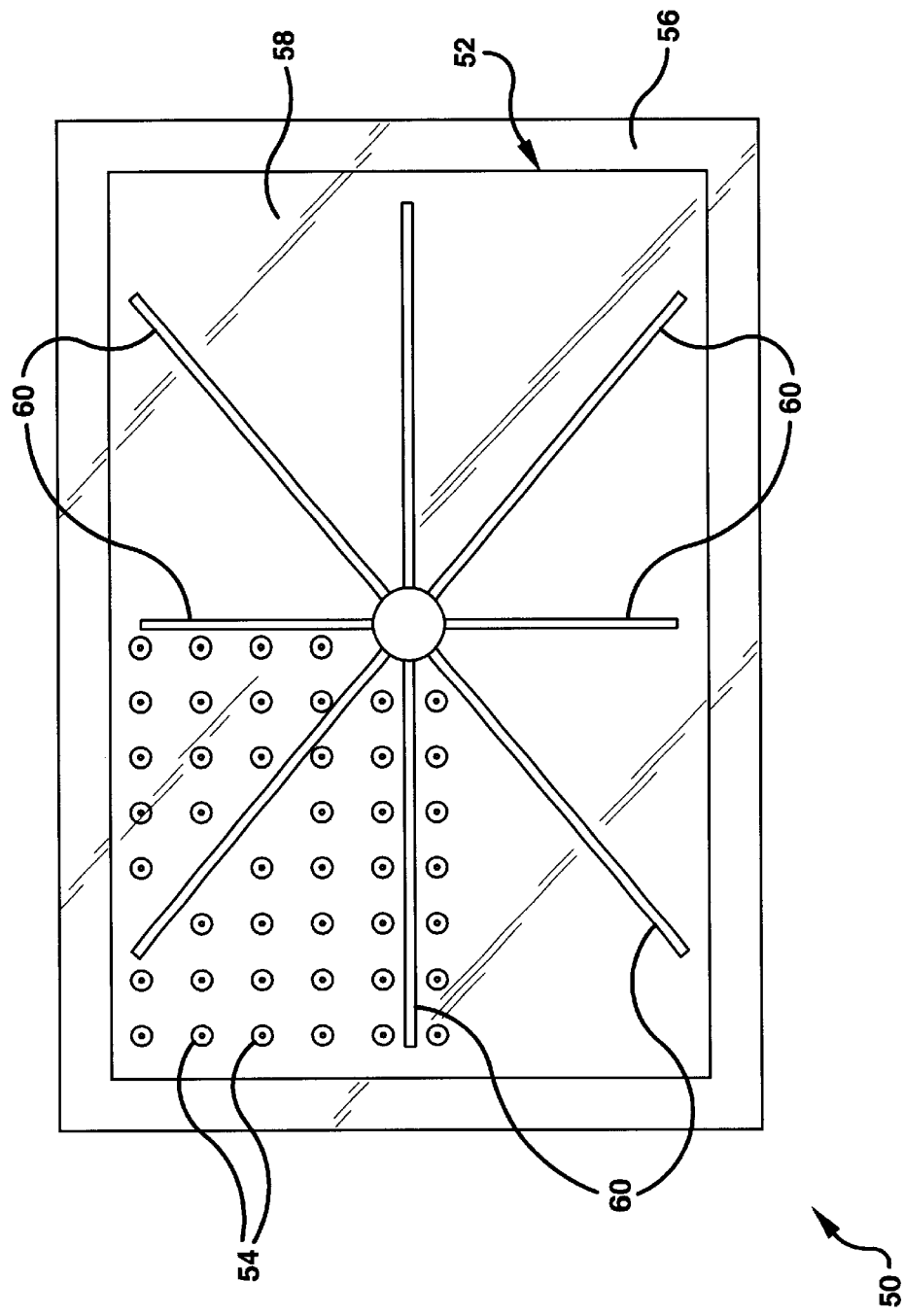
FIG. 6 is a bottom view of the microabrader in a further embodiment, showing the microabrader needles and a dry pharmaceutical agent.

A further embodiment of the microabrader device is illustrated in FIG. 6. Referring to FIG. 6, the microabrader device 50 includes a base 52 having an array of microneedles 54 for abrading the skin. The microneedles are substantially solid with no openings or passages through the microneedles. The base is generally flat, although in further embodiments the base and the abrading surface can be curved, convex or concave.

A flexible sheet material having an adhesive layer 56 is applied over the upper surface of the base 52 and is attached to the base by the adhesive. As shown in FIG. 6, the sheet is larger than the dimension of the base and overlaps on each of the sides to provide an exposed area of adhesive for attaching the device to the skin of a patient. A removable cover can be attached to the device to protect the microneedles until ready for use.

Referring to FIG. 6, the bottom surface 58 of the base 52 is provided with a plurality of channels 60 formed in the bottom surface. The channels 60 extend from the center outwardly toward the edges of the base 52. In the embodiment illustrated, eight channels are illustrated, although additional channels can be provided. The channels 60 are illustrated as being straight, although in further embodiments, the channels can be curved and branched depending on the dimension of the base 52, the distribution of the microneedles 54. A dried or lyophilized substance, such as a pharmaceutical agent or drug can be provided in the channels.

In use, the base 52 is applied to the skin of the patient being treated so that the microneedles 54 penetrate the stratum corneum. The base is rubbed on the skin according to the method previously discussed to abrade the outermost portion of the stratum corneum of the skin and thereby enhance the penetration of the microneedles into the stratum corneum and the delivery of the pharmaceutical agent to the tissue. The base is then attached to the skin by the adhesive 56 to allow the pharmaceutical agent to pass through the stratum corneum for delivering the substance to the patient.

The microabrader device of the invention is generally designed to be a disposable, single-use device. The device can be used safely and effectively for preparing the delivery site for delivery of a substance for absorption by a patient. The device is particularly suitable for preparing the skin for introducing small amounts of a vaccine antigen for presentation to the Langerhans cells. The length, width and spacing of the microneedles can vary depending on the pharmaceutical agent being administered or required to penetrate the stratum corneum to the optimum depth for the specific pharmaceutical agent being administered.

The microabrader used in conjunction with an intradermal delivery device provides a reliable way to deliver individual and multiple pharmaceutical agents in small doses by an intradermal route. The microneedles of the device limit the penetration of the needles to prevent inadvertent deep penetration into the tissue as in conventional needles. The microneedles are also less painful to the patient and exhibit a lower incidence of skin necrosis common with some DNA vaccines. The delivery device can have multiple chambers to administer multiple vaccines and pharmaceutical agents simultaneously without reformulation or combination of the pharmaceutical agents. Administering the pharmaceutical agents into the stratum corneum provides efficient absorption into the bloodstream, thereby reducing the dose of the vaccine. The device is particularly suitable for DNA vaccines that may be a stable dry product.

The following non-limiting examples demonstrate the advantages of abrading the skin in combination with transdermal delivery devices.

EXAMPLE 1

A microabrader having a surface area of about 1 $cm^2$ is provided with a plurality of microneedles having a length of about 250 microns. The microneedles were arranged in a plurality of uniform rows and columns to provide a needle density of about 200 needles per cm².

The microabrader was gently placed on the back of guinea pigs and moved across the skin to produce an abraded area of about 4 cm². The microabrader was scraped along the same path several times to produce an abraded delivery site. The microabrader was removed and a commercially available anesthetic cream sold under the trademark EMLA was applied. The anesthetic cream was applied to a second group of guinea pigs in the same location without abrading.

The topical anesthetic was allowed to contact the skin for one hour before conducting the test for anesthesia. Each guinea pig received five controlled stimuli on the treatment site. In the negative control group, the test site was defined by a similar circle drawn in the same area of the back that was treated in the experimental animals. The controlled stimuli consisted of touching the treated areas with one or more standard monofilaments (von Frey filaments). Preliminary validation studies were conducted to select one filament for use in the testing. This was the smallest filament (least intense stimulus) that would produce twitches with a 100% response rate with no anesthetic. The 4.08 gauge filament was selected and used in these tests.

The degree of topical anesthesia in the treated site was determined by recording the number of twitches observed in response to five stimuli to the site. The anesthesia was calculated as the percent of stimuli not eliciting a response. Thus, five stimuli to a site which produced three twitches translates to a percent anesthesia of 100×2/5=40%. The results for the animals were averaged for each determination.

Figure 7:
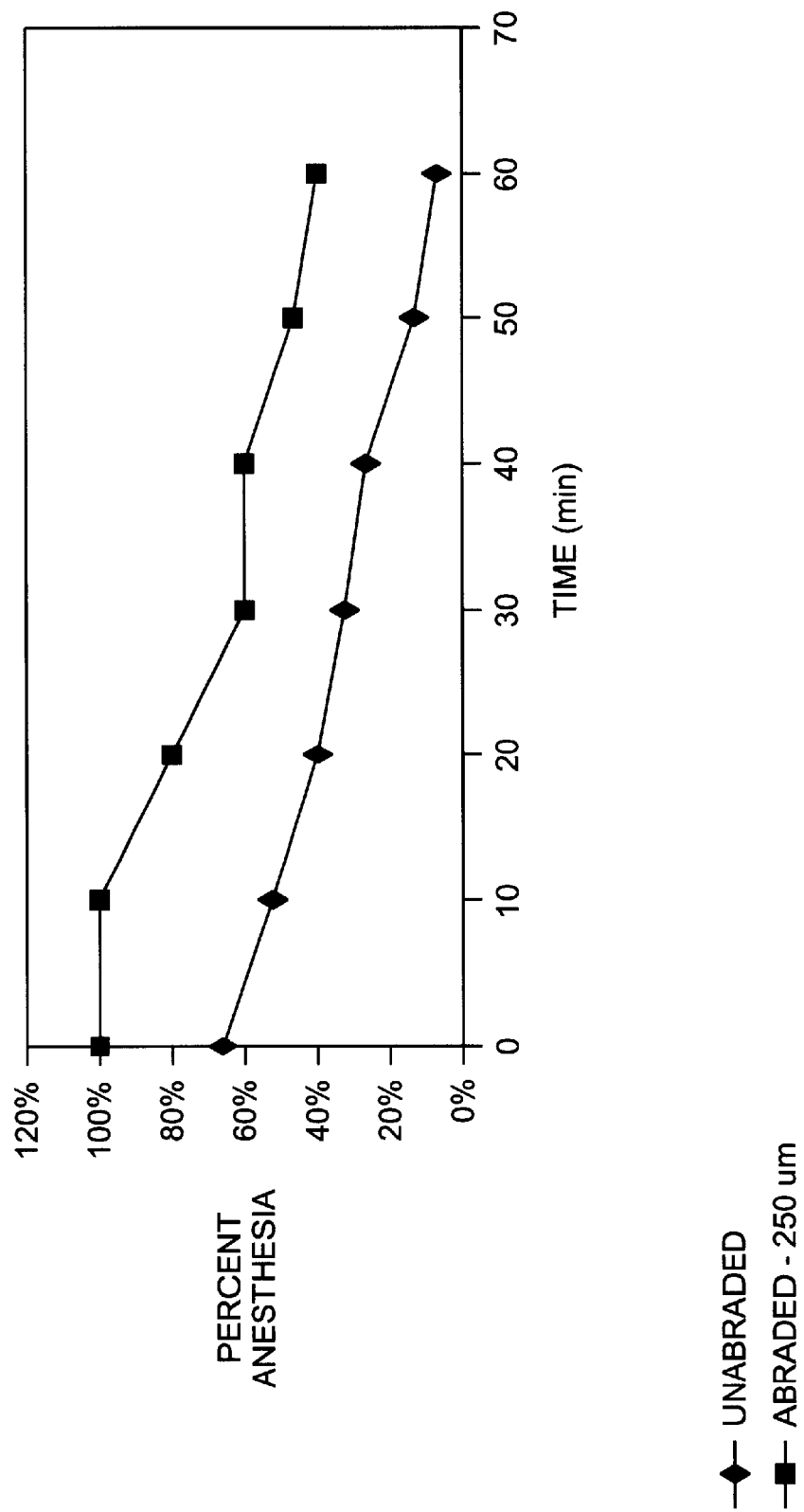
FIG. 7 is a graph comparing the percentage of anesthesia by delivery of a topical anesthetic cream on abraded and unabraded delivery sites.

The degree of anesthesia was measured after the one hour application and repeated every 10 minutes for another hour. The results are shown in the graph of FIG. 7. The results show that after treatment with the anesthetic (time 0) the abraded delivery site exhibited 100% anesthesia compared to about 65% for the unabraded site. The data also shows very good anesthesia after a total elapsed time of 30–40 minutes.

EXAMPLE 2

A microabrader having microneedles of about 200 microns in length was used to abrade the skin of guinea pigs in preparation for delivery of the anesthetic lidocaine by iontophoresis.

Iontophoresis patches were applied to the abraded delivery site to deliver lidocaine for 5 minutes at 1.8 mA. The control delivery sites without abrasion were treated with an identical lidocaine iontophoresis device for 5 minutes. The anesthesia obtained by the twitch method of Example 1 is presented in the graph of FIG. 8. The iontophoresis current was discontinued after 5 minutes and the extent of anesthesia measured for 1 hour. As shown by the data of FIG. 8, iontophoresis applied to a microabrasion site attained 100% anesthesia immediately after application, while the same iontophoresis without abrading attained about 50% anesthesia.

Figure 8:
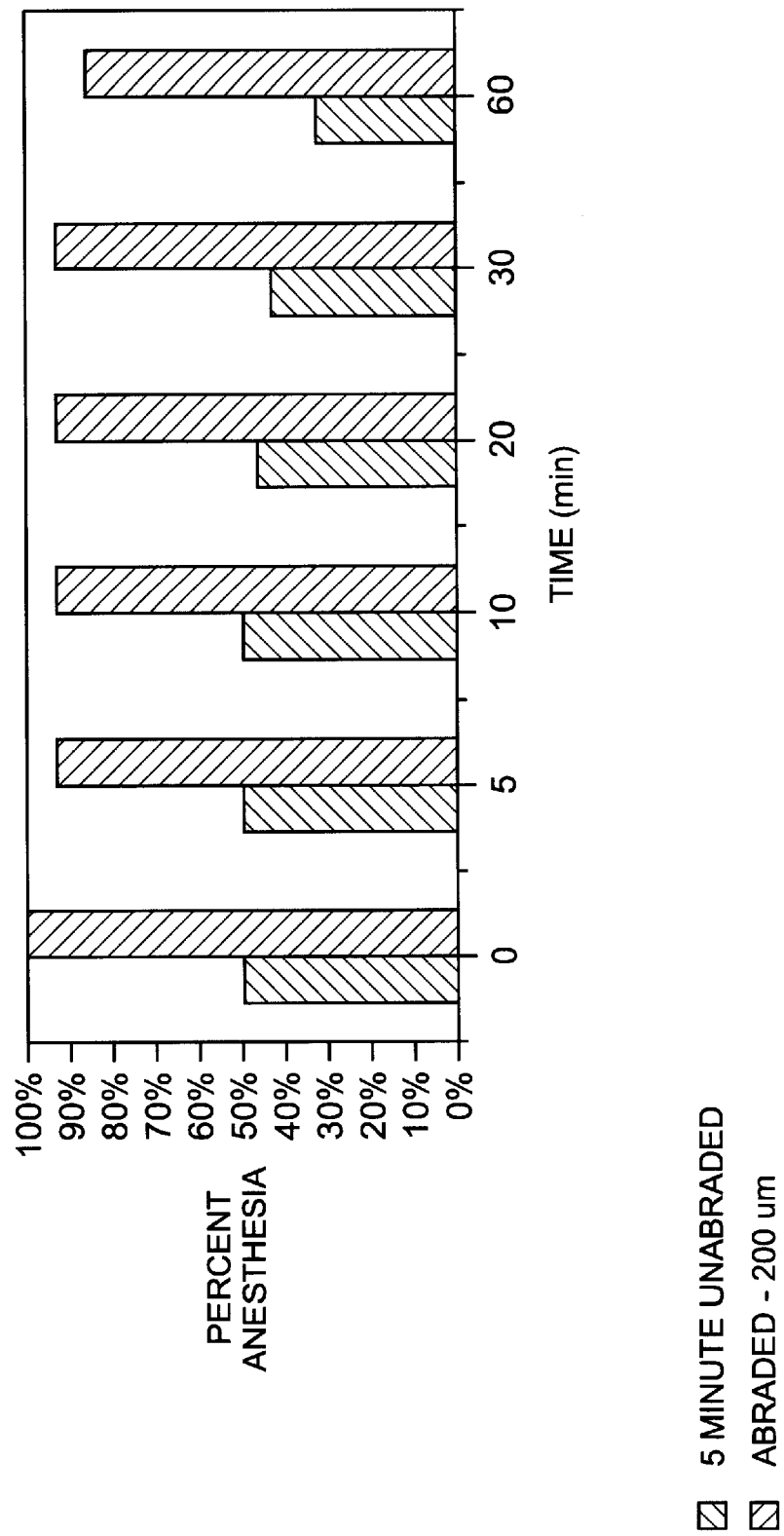
FIG. 8 is a graph comparing the effects of an anesthetic using an iontophoretic device on abraded and unabraded delivery sites.

As shown in the graph of FIG. 8, the abraded site maintained a higher percent anesthesia than the site without abrasion.

EXAMPLE 3

This example evaluates the dose of lidocaine in the tissue. Lidocaine iontophoresis was conducted on anesthetized Yorkshire pigs using patches spiked with $^{14}$C lidocaine. Four abraders were selected having different microneedle lengths and shapes as follows: 100 microns with sharp points; 100 microns with blunt, flat tips; 200 microns with sharp points; and 200 microns with blunt, flat tips.

A delivery site was prepared on the pigs by abrading the skin with each of the microabraders and the patches were applied at about 1.8 mA. The radiolabeled lidocaine that was delivered to the pig was imaged on tape strips and assayed in the skin underlying the patch application site. The tape strips qualitatively show enhancement of lidocaine delivery with abrasion.

Figure 9:
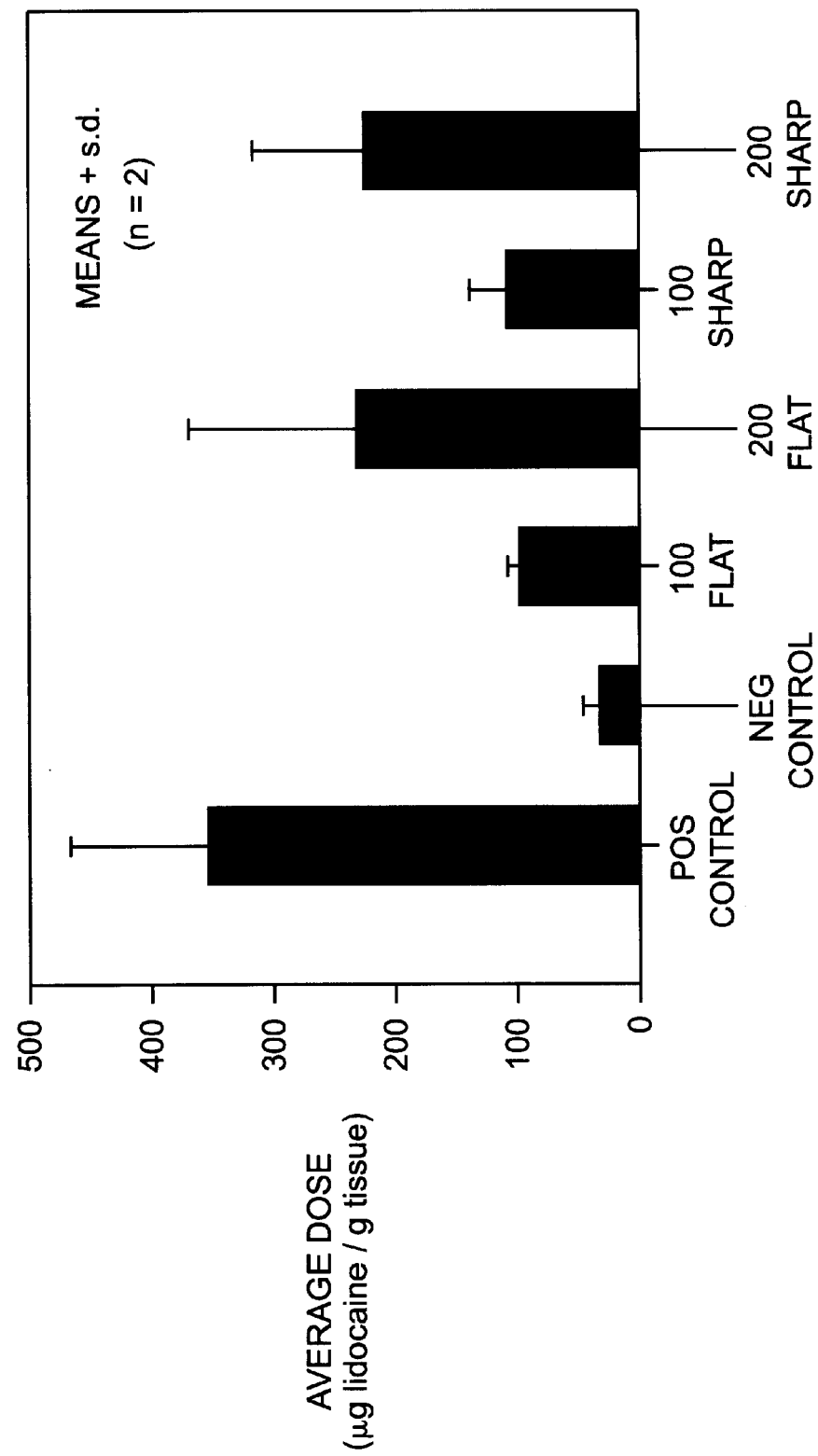
FIG. 9 is a graph showing the dose absorbed by the skin in relation to the microabrader needle length and shape of the tip.

The treated skin was biopsied and cut into sections that were then dissolved and assayed for radiolabeled lidocaine with liquid scintillation counting. The average doses were determined by averaging the tissue doses for each section of the sites from the two applications. The results shown in FIG. 9 indicate that the abrader length affects the tissue dose. Compared to the control skin without abrasion, the enhancement was about three times for the 100-micron abraders, and about seven times for the 200-micron abraders.

EXAMPLE 4

This example compares the effects of the current on the delivery of the anesthetic using iontophoresis on abraded and unabraded delivery sites. Delivery sites were prepared by abrading the skin as in Example 1. An iontophoretic device as in Example 2 was applied to an abraded site and to an unabraded site to apply lidocaine at 2 mA. Identical abraded and unabraded delivery sites were prepared and the lidocaine applied using the iontophoretic device at 4 mA. The percent anesthesia as shown in FIG. 10 indicates that the delivery is directly proportional to the applied current and that abrading the skin prior to delivery increases anesthesia at all current levels.

EXAMPLE 5

This example compares the subcutaneous injection of a Parathyroid hormone referred to as PTH(1–34) with delivery by an iontophoretic patch. PTH dosing solutions were prepared at 100 µg/ml in normal saline. A 25 µg dose was delivered to the test animal as a 0.25 ml injection into pinched loose skin halfway down the dorsal mid-line posterior to the last rib.

A two-compartment style iontophoretic patch was loaded with a solution of the drug immediately prior to applying to the skin. The patches had a 1/32-inch thick reservoir and an active area of 1.0, 2.0 or 4.0 cm². The volume of the drug solution applied to each patch was 50, 100 and 200 µl, respectively. The patches contained an upper electrode compartment with a silver anode in a hydrogel with a particulate cation exchange material in the sodium ion form. The lower drug reservoir compartment had an absorbent 1/32 inch thick hydrophilic porous medium. The two compartments were separated by a size exclusion membrane. The current for these experiments was applied for 4 hours at 0.5 mA/cm².

The drug solution for the iontophoretic patch was prepared in 10 mM acetic acid, 5 mM NaOH and 30% glycerin.

The microabraders were made by a wet etching process from a silicon wafer. The microabraders were uniform two-dimension arrays of solid microneedles integral with a base. The microneedles had sharp points and a conical shape with a length of about 200 microns. The microabrader had a surface area of about 1 cm² and about 200 microneedle points. The skin was cleaned with 70% isopropyl alcohol.

The microabrader was swiped over the cleaned area in a grid-like pattern for about 15 seconds to produce an abraded delivery site of about 4–5 cm². A small amount of skin was observed flaking off. No skin irritation was observed.

The iontophoretic patches were applied over the abraded delivery site. The amount of PTH in the plasma was monitored over a period of 4 hours. The results as shown in the graph of FIG. 11 indicate a similar increase in PTH blood levels over time compared to subcutaneous injection.

EXAMPLE 6

This example demonstrates the effect of microabrasion on the extraction of analytes through the skin during iontophoresis. In this example, the extraction was evaluated using sodium fluorescein as a fluorescent probe. The extraction was measured from a weanling swine using iontophoresis on normal and abraded sites. Test conditions were evaluated on sites with iontophoresis with abrasion, iontophoresis without abrasion, and no iontophoresis with no abrasion.

Animal preparation: A weanling swine was anesthetized and the test area on its side was clipped and washed with saline. Sites for two sets of iontophoretic patches (one anode and one cathode in each set) were identified and marked. The first site served as the non-abraded control, and the second site was abraded using five light passes with a silicon micro-abrader having an array of microneedles of about 200 microns in length.

Patch Design: Each iontophoretic set comprised an anode and a cathode patch. The anode patch consisted of a 2 cm² silver metal mesh pressed onto 4 cm² of 1/32" Porex (sintered, porous polyethylene). The cathode patch consisted of a 2 cm² chlorided silver mesh with 4 cm² of 1/32" Porex. Each assembly was covered with an overlay of adhesive-coated polyethylene. 200 microliters of normal saline was added to each Porex disc, and the patches were applied to the sites on the animal. A single Porex disc was used as a non-abraded, non-iontophoretic control. The entire experimental procedure was repeated on the other side of the animal to give an N of 2 for each case.

Impedance and TEWL: Triplicate Transcutaneous Epidermal Water Loss (TEWL) and Impedance determinations were made on all sites designated for patch placement before and after abrasion. TEWL increased by approximately 10-fold and impedance was reduced by 35–60% indicating that the skin barrier function was reduced by abrasion.

Experimental procedure: At time zero, the animal was given a bolus injection of 6 mg/kg sodium fluorescein (in an 18.1 kg swine) using the procedure outlined by Eppstein et al. in *Diabetes Technology & Therapeutics*, Vol. 1, No. 1, 1999, pp. 21–27. Approximately 7 minutes after injection, 600 microamps of current was passed through each iontophoretic patch pair for 10 minutes. At the end of the application, all patches were removed and the fluid from each patch was extracted and analyzed for fluorescence. Fluid was removed from the Porex by centrifugation followed by a methanol wash and a second centrifugation. The supernatant was reconstituted to the original load volume and fluorescence was determined on SLM Aminco Fluorimeter (excitation=493.5 nm; emission=520 nm).

Results: Fluorescein recovery results are shown in Table 1 below and the graph of FIG. 12. Table 1 shows the measured fluorescence emission and the concentration of samples obtained at each sampling site. The data show that iontophoresis increases extraction of fluorescein relative to passive extraction, and fluorescein is preferentially driven in the anode relative to the cathode. Moreover, the data show that abrasion in combination with iontophoresis enhances extraction of fluorescein more than three-fold in the anode and two-fold in the cathode.

TABLE 1

| Samples Extracted from Patches ISF Samples Max Emission | | | | | |
|---|---|---|---|---|---|
| | Abraded | | Non-Abraded | | |
| | Cathode | Anode | Cathode | Anode | Control |
| Side 1 | 6337 | 15800 | 2761 | 4936 | 1264 |
| Side 2 | 5716 | 12540 | 1484 | 3846 | 1212 |
| Samples Conc. Mm | | | | | |
| | Abraded | | Non-Abraded | | NO-IONT |
| | Cathode | Anode | Cathode | Anode | Control |
| Side 1 | 0.01007 | 0.02511 | 0.00439 | 0.00784 | 0.00201 |
| Side 2 | 0.00908 | 0.01993 | 0.00236 | 0.00611 | 0.00193 |
| AVG | 0.00958 | 0.02252 | 0.00337 | 0.00698 | 0.00197 |

While several embodiments have been shown to illustrate the present invention, it will be understood by those skilled in the art that various changes and modifications can be made therein without departing from the scope of the invention as defined in the appended claims.

What is claimed is:

1. A method for the delivery of a substance to a patient, said method comprising:
   positioning a microabrader at a delivery site on the skin of a patient, said microabrader having a support and a plurality of microneedles coupled to said support, each of said microneedles having a length greater than the thickness of the stratum corneum;
   moving said microabrader across the skin of the patient to allow the microneedles to penetrate into the stratum corneum substantially without piercing the stratum corneum and thereby abrade said stratum corneum at said delivery site to increase the permeability of said skin to said substance; and
   applying said substance to said delivery site to transfer said substance through the stratum corneum and into said skin.

2. The method of claim 1, wherein said microneedles are about 50 to about 250 microns in length.

3. The method of claim 1, wherein said microneedles are arranged in an array of columns and rows and are substantially uniformly spaced apart.

4. The method of claim 1, wherein each of said microneedles has a substantially frustoconical shape terminating in a blunt tip.

5. The method of claim 1, wherein said moving step comprises moving said microabrader in one direction in a substantially straight line to form a plurality of spaced-apart grooves on the skin.

6. The method of claim 5, comprising the further steps of repositioning said microabrader at said delivery site and again moving said microabrader in said straight line.

7. The method of claim 1, comprising the further steps of removing said microabrader from said delivery site, and applying a drug delivery device to said delivery site.

8. The method of claim 7, wherein said drug delivery device comprises an iontophoresis device.

9. The method of claim 1, wherein said abraded delivery site comprises an area of skin having a plurality of substantially parallel grooves separated by peaks.

10. The method of claim 7, wherein said drug delivery device comprises a passive delivery device.

11. The method of claim 1, wherein each of said microneedles has a plurality of side walls extending from said support and terminating in a blunt tip.

12. The method of claim 11, wherein said blunt tip has a substantially flat face that is substantially parallel to said support.

13. The method of claim 12, wherein said flat face of said tip joins each of said side walls along an abrading edge.

14. The method of claim 11, wherein each of said side walls is joined to an adjacent side wall along an abrading edge.

15. A method of treating the skin of a patient to enhance transdermal delivery of a substance or the withdrawal of said substance from the body of said patient, said method comprising:

positioning a microabrader at a treatment site on the skin of said patient, said microabrader having a plurality of microneedles, each of said microneedles having a length greater than the thickness of the stratum corneum; and moving said microabrader across the skin of the patient to allow said microneedles to penetrate into said stratum corneum substantially without piercing said stratum corneum and thereby abrade said skin and form an abraded area, said abraded area having a plurality of grooves formed in said stratum corneum from abrasion by said microneedles.

16. The method of claim 15, wherein said microneedles are about 50 to about 250 microns in length, are arranged in a plurality of columns and rows, and are substantially uniformly spaced apart.

17. The method of claim 15, wherein each of said microneedles has a substantially frustoconical shape terminating in a blunt tip.

18. The method of claim 15, comprising the further steps of repositioning said microabrader at said delivery site and again moving said microabrader over the same area of the skin.

19. The method of claim 15, wherein each of said microneedles has a plurality of side walls extending from a planar support and terminating at a blunt tip.

20. The method of claim 19, wherein said blunt tip has a substantially flat face that is substantially parallel to said planar support.

21. The method of claim 20, wherein said flat face of said tip joins each of said side walls along an abrading edge.

22. The method of claim 19, wherein each of said side walls is joined to an adjacent side wall along an abrading edge.

23. A method of treating the skin of a patient to reduce the electrical resistance of the skin at a treatment site, said method comprising:

positioning a microabrader having a plurality of microneedles at said treatment site, each of said microneedles having a length greater than the thickness of the stratum corneum;

moving said microabrader across the skin of the patient to allow the microneedles to penetrate into the stratum corneum substantially without piercing the stratum corneum and thereby abrade said stratum corneum on said treatment site;

placing a signal electrode at or near-the prepared treatment site; and recording at least one signal from said electrode.

24. The method of claim 23, wherein said abrading step abrades the stratum corneum on the treatment site substantially without piercing the stratum corneum.

25. The method of claim 23, comprising the step of moving the microabrader on the skin of the patient to form a plurality of grooves in the stratum corneum, said grooves having a depth to penetrate the stratum corneum substantially without piercing the stratum corneum.

* * * * *